United States Patent
Dalton et al.

(10) Patent No.: US 6,258,864 B1
(45) Date of Patent: *Jul. 10, 2001

(54) POLYMER FOAM CONTAINING CHEMICALLY MODIFIED CARBONACEOUS FILLER

(75) Inventors: Dennis M. Dalton, Derry, NH (US); David A. Kinsman, Allston, MA (US); Lynn M. Krajkowski, Waltham, MA (US); Adam L. MacKay, Arlington, MA (US)

(73) Assignee: Cabot Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 38 days.

(21) Appl. No.: 09/317,287

(22) Filed: May 24, 1999

Related U.S. Application Data
(60) Provisional application No. 60/116,500, filed on Jan. 20, 1999.

(51) Int. Cl.$^7$ .................................................. C08J 9/00
(52) U.S. Cl. ........................... 521/82; 521/99; 521/155; 523/215; 524/80
(58) Field of Search ............... 521/82, 99, 155; 523/215; 524/80

(56) References Cited

U.S. PATENT DOCUMENTS

| | | |
|---|---|---|
| 1,283,229 | 10/1918 | Lee . |
| 3,015,645 | 1/1962 | Tyler . |
| 3,122,520 | 2/1964 | Lentz . |
| 3,455,839 | 7/1969 | Rauner . |
| 3,486,967 | 12/1969 | Fisher . |
| 3,499,848 | 3/1970 | Weisman . |
| 3,556,158 | 1/1971 | Schneider . |
| 3,593,437 | 7/1971 | Kogert . |
| 3,634,604 | 1/1972 | Lusk . |
| 3,640,920 | 2/1972 | Cear . |
| 3,776,741 | 12/1973 | Bockstie . |
| 3,800,031 | 3/1974 | Sale et al. . |
| 3,803,046 | 4/1974 | Winyall et al. . |
| 3,996,188 | 12/1976 | Laur . |
| 4,010,123 | 3/1977 | Blunt . |
| 4,036,933 | 7/1977 | Laufer . |
| 4,045,380 | 8/1977 | Blunt . |
| 4,048,105 | 9/1977 | Salisbury . |
| 4,094,685 | 6/1978 | Lester . |
| 4,108,791 | 8/1978 | Wasilczyk . |
| 4,137,199 | 1/1979 | Brown . |
| 4,152,503 | 5/1979 | Short . |
| 4,169,926 | 10/1979 | McDaniel . |
| 4,231,901 | 11/1980 | Berbeco . |
| 4,278,770 | 7/1981 | Chandalia . |
| 4,279,879 | 7/1981 | Winyall . |
| 4,282,329 | 8/1981 | von Bonin . |
| 4,303,641 | 12/1981 | DeWolf, II . |
| 4,305,796 | 12/1981 | Gagliardi . |
| 4,307,127 | 12/1981 | Shah . |
| 4,327,065 | 4/1982 | von Dardel . |
| 4,344,800 | 8/1982 | Lutz . |
| 4,360,610 | 11/1982 | Murray et al. . |
| 4,398,527 | 8/1983 | Rynbrandt . |
| 4,432,956 | 2/1984 | Zarzychi et al. . |
| 4,434,253 | 2/1984 | Rys-Sikora . |
| 4,442,160 | 4/1984 | Toba et al. . |
| 4,442,228 | 4/1984 | Leupold et al. . |
| 4,443,253 | 4/1984 | Weir et al. . |
| 4,444,673 | 4/1984 | Joshi et al. . |
| 4,493,788 | 1/1985 | Fujie et al. . |
| 4,500,659 | 2/1985 | Kroupa et al. . |
| 4,505,973 | 3/1985 | Neet et al. . |

(List continued on next page.)

FOREIGN PATENT DOCUMENTS

| | | |
|---|---|---|
| 1 223 424 | 6/1987 | (CA) . |
| 2 024 810 | 5/1970 | (DE) . |
| 2 032 174 | 1/1972 | (DE) . |
| 2 028 353 | 8/1979 | (DE) . |
| 36 29 390 | 2/1988 | (DE) . |
| 195 33 565 | 3/1997 | (DE) . |
| 196 49 279 | 6/1998 | (DE) . |
| 197 02 781 | 7/1998 | (DE) . |
| 197 06 030 | 8/1998 | (DE) . |
| 197 28 543 | 1/1999 | (DE) . |
| 198 12 856 | 9/1999 | (DE) . |
| 0 026 920 A2 | 10/1980 | (EP) . |

(List continued on next page.)

OTHER PUBLICATIONS

Barringer, C. M. Designing Rigid Urethane Foams for Low Moisure Permeability, *SPE Journal*, Nov. 1959.

Gluck, et al., Carbon Black–Filled Foam Insulations, 32nd Annual Polyurethane Technical/Marketing Conference, Oct. 1–4, 1989.

Knox, R.E., Insulation Properties of Fluorocarbon Expanded Rigid Urethane Foam, *Ashrae Journal*, Oct. 1962.

LaBras, L. R., Recent Developments in Rigid Urethane Foams, *SPE Journal*, Apr.1960.

Saunders & Frisch, *Polyurethanes: Chemistry and Technology*, 1964.

Research Disclosure, p. 42551, Sep. 1999.
Research Disclosure, p. 42562, Sep. 1999.

*Primary Examiner*—Morton Foelak

(57) ABSTRACT

Polymer foam compositions comprise polymer foam and chemically modified carbonaceous filler, specifically, carbonaceous filler having polymer moieties chemically bonded to the carbonaceous particulates. Exemplary carbonaceous fillers include carbon black, activated carbon, graphite, carbon fibers, fibrils and the like. The polymer moieties have a valence orbital bond to the carbonaceous particulate, such as an ionic or covalent bond. The chemical bond survives shear forces and the like, such as would be encountered by filler material in a reaction injection molding process for the manufacture of filled polyurethane foam insulation panels.

12 Claims, No Drawings

U.S. PATENT DOCUMENTS

| | | |
|---|---|---|
| 4,517,319 | 5/1985 | Reske et al. . |
| 4,525,297 | 6/1985 | Yamane et al. . |
| 4,547,529 | 10/1985 | Lee et al. . |
| 4,548,958 | 10/1985 | Bauman et al. . |
| 4,567,212 | 1/1986 | Bauman et al. . |
| 4,572,869 | 2/1986 | Wismer et al. . |
| 4,596,725 | 6/1986 | Kluth et al. . |
| 4,603,073 | 7/1986 | Renalls et al. . |
| 4,610,863 | 9/1986 | Tewari et al. . |
| 4,619,908 | 10/1986 | Cheng et al. . |
| 4,621,106 | 11/1986 | Francalossi et al. . |
| 4,661,533 | 4/1987 | Stobby . |
| 4,711,911 | 12/1987 | Blount . |
| 4,731,401 | 3/1988 | Moteki et al. . |
| 4,745,144 | 5/1988 | Itoh et al. . |
| 4,760,099 | 7/1988 | Canaday et al. . |
| 4,766,000 | 8/1988 | Sobus . |
| 4,767,795 | 8/1988 | Adam et al. . |
| 4,776,867 | 10/1988 | Onorato et al. . |
| 4,778,636 | 10/1988 | Krieg et al. . |
| 4,795,763 | 1/1989 | Gluck et al. . |
| 4,891,399 | 1/1990 | Ohkawa et al. . |
| 4,954,327 | 9/1990 | Blount . |
| 5,010,112 | 4/1991 | Glicksman et al. . |
| 5,015,448 | 5/1991 | Vorlop et al. . |
| 5,069,816 | 12/1991 | DeSantis et al. . |
| 5,071,703 | 12/1991 | Weber et al. . |
| 5,075,343 | 12/1991 | Blount . |
| 5,078,919 | 1/1992 | Ashley et al. . |
| 5,100,923 | 3/1992 | Hintz et al. . |
| 5,102,919 | 4/1992 | Swab . |
| 5,110,840 | 5/1992 | Blount . |
| 5,122,291 | 6/1992 | Wolff et al. . |
| 5,122,305 | 6/1992 | Ashley et al. . |
| 5,130,110 | 7/1992 | Rouet et al. . |
| 5,137,190 | 8/1992 | Plaud . |
| 5,137,659 | 8/1992 | Ashley et al. . |
| 5,137,930 | 8/1992 | Soukup . |
| 5,141,968 | 8/1992 | Dietrich et al. . |
| 5,149,722 | 9/1992 | Soukup . |
| 5,158,758 | 10/1992 | Chieng et al. . |
| 5,169,926 | 12/1992 | Keijsper et al. . |
| 5,192,607 | 3/1993 | Soukup . |
| 5,210,105 | 5/1993 | Paquet et al. . |
| 5,215,733 | 6/1993 | Potter . |
| 5,240,647 | 8/1993 | Ashley et al. . |
| 5,258,418 | 11/1993 | Krueger et al. . |
| 5,260,347 | 11/1993 | Krueger et al. . |
| 5,275,796 | 1/1994 | Tillotson et al. . |
| 5,328,645 | 7/1994 | Lin et al. . |
| 5,334,337 | 8/1994 | Voelker et al. . |
| 5,338,783 | 8/1994 | Olsen . |
| 5,340,866 | 8/1994 | Evans . |
| 5,373,026 | 12/1994 | Bartz et al. . |
| 5,380,464 | 1/1995 | McGee et al. . |
| 5,397,807 | 3/1995 | Hitchcock et al. . |
| 5,397,808 | 3/1995 | Doerge et al. . |
| 5,409,683 | 4/1995 | Tillotson et al. . |
| 5,461,098 | 10/1995 | Hitchcock et al. . |
| 5,474,806 | 12/1995 | Morgan et al. . |
| 5,506,302 | 4/1996 | Shiono et al. . |
| 5,525,660 | 6/1996 | Shiono et al. . |
| 5,529,777 | 6/1996 | Andrianov et al. . |
| 5,531,929 | 7/1996 | Kobayashi . |
| 5,540,767 | 7/1996 | Ronlan . |
| 5,543,082 | 8/1996 | McGee et al. . |
| 5,554,662 | 9/1996 | Sanders et al. . |
| 5,558,849 | 9/1996 | Sharp . |
| 5,565,497 | 10/1996 | Godbey et al. . |
| 5,569,513 | 10/1996 | Fidler et al. . |
| 5,571,847 | 11/1996 | Hitchcock et al. . |
| 5,587,107 | 12/1996 | Schwertfeger et al. . |
| 5,604,265 | 2/1997 | De Vos et al. . |
| 5,616,628 | 4/1997 | von Bonin et al. . |
| 5,633,584 | 5/1997 | Maryanski et al. . |
| 5,647,962 | 7/1997 | Jansen et al. . |
| 5,651,921 | 7/1997 | Kaijou . |
| 5,680,713 | 10/1997 | Forbert et al. . |
| 5,683,528 | 11/1997 | Partlow et al. . |
| 5,698,606 | 12/1997 | De Vos et al. . |
| 5,705,535 | 1/1998 | Jansen et al. . |
| 5,708,069 | 1/1998 | Burns et al. . |
| 5,709,058 | 1/1998 | Shaw . |
| 5,801,210 | 9/1998 | Radovich et al. . |
| 5,804,648 | 9/1998 | Slack . |
| 5,859,081 | 1/1999 | Duffy . |
| 5,993,707 | 11/1999 | Chaudhary et al. . |

FOREIGN PATENT DOCUMENTS

| | | |
|---|---|---|
| 0 072 536 B1 | 8/1982 | (EP) . |
| 0 091 828 B1 | 4/1983 | (EP) . |
| 0 208 809 A2 | 10/1985 | (EP) . |
| 0 186 887 A2 | 12/1985 | (EP) . |
| 0 256 252 A1 | 6/1987 | (EP) . |
| 0 293 060 A2 | 1/1988 | (EP) . |
| 0 148 521 B1 | 1/1990 | (EP) . |
| 0 434 225 B1 | 11/1990 | (EP) . |
| 0 653 377 A1 | 11/1993 | (EP) . |
| 0 638 346 A2 | 7/1994 | (EP) . |
| 0 657 517 A1 | 12/1994 | (EP) . |
| 0 672 635 A1 | 3/1995 | (EP) . |
| 0 702 119 A2 | 9/1995 | (EP) . |
| 0 704 492 A2 | 9/1995 | (EP) . |
| 0 798 371 A1 | 3/1996 | (EP) . |
| 0 745 648 A2 | 5/1996 | (EP) . |
| 0 767 199 A1 | 10/1996 | (EP) . |
| 0 774 285 A2 | 11/1996 | (EP) . |
| 0 802 229 A2 | 4/1997 | (EP) . |
| 0 802 230 A2 | 4/1997 | (EP) . |
| 0 884 338 A1 | 6/1998 | (EP) . |
| 0 889 082 B1 | 6/1998 | (EP) . |
| 0 930 323 A1 | 1/1999 | (EP) . |
| 0 939 071 A1 | 2/1999 | (EP) . |
| 0 943 667 A1 | 3/1999 | (EP) . |
| 1 447 850 | 6/1966 | (FR) . |
| 2 179 174 | 4/1973 | (FR) . |
| 2 288 610 | 5/1976 | (FR) . |
| 2 489 416 | 3/1982 | (FR) . |
| 2 512 736 | 3/1983 | (FR) . |
| 2 028 353 | 3/1980 | (GB) . |
| 2 064 485 | 6/1981 | (GB) . |
| 2 113 228 | 8/1983 | (GB) . |
| 2 146 345 | 4/1985 | (GB) . |
| 2 298 424 | 9/1996 | (GB) . |
| 2 324 798 | 11/1998 | (GB) . |
| 57-147510 | 9/1982 | (JP) . |
| 6-281414 | 10/1994 | (JP) . |
| 10-195225 | 10/1998 | (JP) . |
| 10-268629 | 10/1998 | (JP) . |
| 10-292104 | 10/1998 | (JP) . |
| 11-279254 | 10/1999 | (JP) . |
| 91/13112 | 9/1991 | (WO) . |
| 94/13721 | 6/1994 | (WO) . |
| 95/15355 | 6/1995 | (WO) . |
| 95/15356 | 6/1995 | (WO) . |
| 97/47691 | * 12/1997 | (WO) . |
| 98/23678 | 6/1998 | (WO) . |
| 99/31176 | 6/1999 | (WO) . |
| 99/47592 | 9/1999 | (WO) . |

* cited by examiner

POLYMER FOAM CONTAINING CHEMICALLY MODIFIED CARBONACEOUS FILLER

This application claims the priority benefit of U.S. provisional application Ser. No. 60/116,500 filed on Jan. 20, 1999, entitled Polymer Foam Containing Chemical Black Filler.

INTRODUCTION

The present invention is directed to improvements in the field of polymer foams, especially closed-cell polymer foams useful for thermal insulation applications and the like, containing surface-modified carbonaceous fillers. This invention also relates to novel compositions useful in the manufacture of such polymer foams.

BACKGROUND

Polymer foams containing filler materials, such as particulate filler materials, are widely known and used. Closed cell rigid polymer foams, especially polyurethane and polyisocyanurate foams containing particulate filler, such as carbon black or other particulate filler, are widely used for thermal insulation purposes. Foams of this type and their use for thermal insulation purposes are disclosed, for example, in U.S. Pat. No. 5,604,265 to DeVos et al. Also, in U.S. Pat. No. 5,373,026 to Bartz et al, polymer foam structures incorporating carbon black filler are taught for thermal insulation purposes.

In polymer foams such as, for example, polyurethane and polyisocyanurate foams, cost reduction and/or thermal insulation improvement can be achieved by improving dispersion of filler material in the foam, by controlling foam cell size, and/or by increasing infrared absorption. The windows of the cell structure are believed to be significantly transparent to infrared radiation. The thermal conductivity of these foams should be improved by increasing the infrared absorption of the cell windows. One way to do this is to add infrared absorbing materials, such as carbon black, to the foam. However, the distribution of carbon black in these foams typically is poor, such that the majority of carbon black resides in the struts of the foam. The windows of the foam may contain little or no carbon black. In fact, it is doubtful that prior work has achieved carbon black concentrations in the windows equivalent to the carbon black concentration found in the struts.

There is a recognized need in the polymer foam industry for foams having improved performance characteristics and/or reduction in the cost and complexity of manufacturing such foams. In certain applications, such as foam insulation and in refrigeration units or other appliances or for architectural insulation, this need has been increased due to the loss of insulation performance caused by the reduction or elimination of halogenated blowing agents. Some substitute blowing agents are found to produce foams having higher thermal conductivity. Hence, there is an increased need for lowering the thermal conductivity of polymer foams suitable for use in various insulation applications, particularly appliance and architectural thermal insulation uses.

It is an object of the present invention to provide improved polymer foams. It is a particular object of the invention to provide polymer foams having lower thermal conductivity, or, the alternative, lower thermal conductivity per unit cost of the foam. In accordance with certain preferred embodiments of the invention, it is an object to provide rigid, closed cell polymer foams incorporating chemically modified carbonaceous filler materials not previously used for such applications, and being suitable for various insulation purposes. These and additional objects and advantages of the present invention will be apparent to those skilled in the art from the following disclosure of the invention and detailed description of certain embodiments.

SUMMARY

In accordance with a first aspect, novel polymer foams are provided which comprise certain chemically modified carbonaceous ("CMC") fillers, that is, chemically modified carbonaceous material dispersed in the polymer foam. The chemically modified carbonaceous filler employed in the present invention comprises carbonaceous particulate material carrying polymer units, optionally being chemically functionalized polymer units, attached to the surface of the particles. As disclosed and described further below, the chemically modified carbonaceous filler comprises carbonaceous material having polymer moiety attachments. In accordance with preferred embodiments, the chemically modified carbonaceous filler is carbonaceous particulate filler, such as carbon black, graphite, activated carbon and the like, which has been surface-modified to attach multiple polymer moieties per filler particle. It is a significant feature that the polymer moieties of a chemically modified carbonaceous filler are directly attached to the surface of the carbonaceous particle by ionic, covalent or equivalent chemical bond. Thus, these filler materials incorporated into the novel polymer foams of the present invention are not mere polymeric coatings on carbonaceous particles which adhere due to van der Waals forces or like attractive forces. Mere coatings of that type have been known in the art, but have not been sufficiently processible and have not provided the needed improvement in thermal insulation performance or cost reduction in commercially manufactured polymer foams. Mere polymeric coatings on carbonaceous filler particulates, such as were obtained by mixing surfactants or other polymers with filler materials, especially if the polymers were of a type and polymer chain length effective to provide substantially improved thermal insulation value in the finished polymer foam, are understood to be stripped in substantial quantity from the carbonaceous particles by the shear forces encountered in commercial polymer foam manufacturing methods. The shear forces encountered in commercial reaction injection molding (RIM) methods, for example, have been found to strip substantial quantities of polymeric coatings from carbonaceous particles, such as carbon black or the like. In contrast, the chemically modified carbonaceous fillers disclosed here for use as fillers in polymer foams, particularly the preferred embodiments, are not stripped in substantial quantity from the carbonaceous particles even under shear forces encountered in commercial polymer foam manufacture. In accordance with preferred embodiments, the chemically modified carbonaceous fillers comprise surface-modified carbonaceous particulate material having chemically bonded polymer moieties, which remain chemically bonded to the carbonaceous particles even under shear forces encountered in RIM processes for manufacturing polyurethane foam insulation and the like. While not wishing to be bound by theory, at least certain preferred embodiments of the chemically modified carbonaceous fillers disclosed here have valence-orbital interactions with the surface of the carbonaceous particle or with a functional group which is itself likewise chemically bonded to the carbonaceous particle. The nature of the surface of the carbonaceous particle covalently or ironically bonded to the polymer moieties is different from the surface of the same particle merely coated with analogous polymer through van der Waals forces or the like.

As disclosed and described further below, the chemically modified carbonaceous filler can be prepared by attaching polymeric moieties to the surface of carbonaceous particulate material. As used here, the polymeric moieties may be a oligomeric. Suitable carbonaceous particulate materials include carbon black, activated carbon, graphite, carbon fibers, fibrils and the like, chemically modified in accordance with any of the chemical modifications further described below. Also, suitable carbonaceous particulate materials include carbon-silica multi-phase material, such as carbon-silica dual-phase particulate filler material available from Cabot Corporation, Boston Mass. under the trademark Ecoblack™, silica-coated carbon black, and/or metal-treated carbon black forming a multi-phase particulate material, all of which may be chemically modified in accordance with the disclosure below. Mixtures of any of the filler materials disclosed here may be used in the filled polymer foams of the invention. Preferably the chemically modified carbonaceous filler is used in an amount of from 0.1 to 18.0 weight percent filler in the final foam composition, more preferably about 1.0 to 12.0 weight percent, e.g., 8.0 wt. %.

In accordance with preferred embodiments, chemically modified carbonaceous filler employed in the polymer foams disclosed here provide improved thermal insulation value higher than corresponding unfilled foams, and higher than corresponding foams containing corresponding carbonaceous filler not having polymer moieties chemically bonded thereto. This improvement may derive, in part, from better processability of the filler, especially better processability using commercially available foam production materials, equipment and techniques, leading to better dispersion of the filler in the foam. In certain embodiments the improvement may derive, in part, in certain embodiments from preferential locating of the chemically modified carbonaceous filler in the "windows" of the foam, as further discussed below.

In accordance with another aspect, rigid, closed cell polymer foams are provided, comprising chemically modified carbonaceous filler disclosed above. Certain preferred embodiments are rigid, closed cell polymer foams with chemically modified carbonaceous fillers, incorporating non-CFC blowing agents and/or the reaction product thereof following manufacture of the foam. In accordance with certain preferred embodiments, polyurethane foams are provided, comprising chemically modified carbonaceous filler dispersed in the foam In accordance with certain preferred embodiments, polyisocyanurate foams are provided, comprising chemically modified carbonaceous filler dispersed in the foam In accordance with certain preferred embodiments, polystyrene foams are provided, comprising chemically modified carbonaceous filler dispersed in the foam.

In accordance with certain preferred embodiments, the chemically modified carbonaceous filler is surface modified carbon black dispersed in either the polyol or the isocyanate reactive component (or both) of a polyurethane foam. system. Chemically modified carbonaceous fillers of this type, when incorporated into rigid closed-cell polyurethane foams in accordance with certain especially preferred embodiments, have higher concentrations in the windows of the foam cells than is achieved using the same polymer system with corresponding untreated carbon black particulate materials. In particular, more of the chemical black particulate filler is at the gas/solid interface in the polyurethane foam. This improved distribution of the filler material results in lower thermal conductivity of the foam in comparison to the same foam containing the corresponding untreated carbon black material. In accordance with certain preferred embodiments, about ninety percent (90%) of the chemically modified carbonaceous filler is present in the struts portion of the foam cells and the remaining about ten percent (10%) is present in the windows of the foam cells. More preferably, only about eighty percent (80%) of the chemically modified carbonaceous filler is present in the struts and at least about twenty percent (20%) is present in the windows. In a further alternative embodiment, the particle density of the chemically modified carbonaceous filler in the windows portion of the foam cells is greater than twenty percent (20%).

In accordance with certain preferred embodiments, closed-cell polymer foam, preferably polyurethane or polyisocyanurate foam, contains chemically modified carbonaceous filler in the form of surface-modified (i.e., specifically, chemically bonded to polymeric moieties, as discussed above) carbon black, activated carbon, graphite, carbon fibers or fibrils, or mixtures of any one or more of them. Preferably such chemically modified carbonaceous fillers provide functional groups effective to preferentially locate the individual particles at the gas/solid interface within the foam, especially in the windows of the foam cells. Preferred functional groups for these chemically modified carbonaceous fillers include, for example, aryl groups, alkyl groups, ketone groups, silane groups, ether groups, fluorinated aryl and alkyl groups, alkyl ester and alkyl ether groups, ketone, pyrrolidinones, polyethers, poly (fluoroether) groups, and poly(dialkylsiloxane) groups.

In accordance with another aspect, closed-cell polymer foam, preferably polyurethane foam, incorporates chemically modified carbonaceous filler modified to impart improved dispersion of the filler in either the isocyanate component or the polyol component of a polyurethane foam system. The improved filler dispersion reduces thermal conductivity of the resulting polyurethane foam. In contrast, when known particulate materials, such as various carbon blacks, are dispersed into a polyurethane foam system, the resulting material typically has an uneven distribution within the foam. In accordance with certain preferred embodiments, chemically modified carbonaceous fillers are used in addition to or in place of some or all such prior known filler materials. More specifically, chemically modified carbonaceous fillers comprising surface modified carbon black, most preferably carbon blacks which have been chemically treated to provide polymeric moieties having organic groups, such as esters or alkyls, impart a beneficial character to the particles yielding improved dispersion in an isocyanate portion of a polyurethane foam system. Chemically modified carbonaceous fillers comprising carbon blacks which have been chemically treated to attach polymer moieties having polar functional groups, such as alcohols, amines and the like, have improved dispersion in a polyol portion of a polyurethane system. Moreover, those chemically modified carbonaceous fillers having alcohol or amine groups will be reactive with an isocyanate portion of the polyurethane system.

In accordance with certain especially preferred embodiments, additional improvement in dispersion and thermal conductivity (that is, better dispersion and lower thermal conductivity) are achieved by combining the aforesaid chemically modified carbonaceous filler materials with surfactants, such as for example, silicone/ethylene oxide or silicone/propylene oxide copolymers.

In accordance with another aspect, polymer reactant materials incorporating chemically modified carbonaceous filler are provided, which are suitable for manufacture of the above disclosed polymer foam products.

Those skilled in the art will recognize from the foregoing disclosure and the following detailed description of certain preferred embodiments, that the present inventive subject matter represents a significant technological advance in the field polymer foams. Especially significant in the field of thermal insulation, the present invention provides filled polymer foams having improved thermal performance characteristics. More particularly, polymer foams incorporating chemical black particulate fillers in accordance at least certain preferred embodiments of the present invention are found to provide improved thermal performance when compared to otherwise comparable foams incorporating a like weight percent carbon black or filler having substantially the same particle size and structure. Other features and advantages of the present invention will be apparent from the following detailed description of certain preferred embodiments.

DETAILED DESCRIPTION OF CERTAIN PREFERRED EMBODIMENTS

It will be apparent from the foregoing, and from the following detailed description of certain preferred embodiments, that the polymer foam disclosed here comprising chemically modified carbonaceous filler will have numerous commercial and industrial applications. Various embodiments will be suitable, for example, as insulation material for housing or other architectural applications and/or as thermal and sound insulation for household and industrial appliances, for example, refrigeration units and the like. It will be within the ability of those skilled in the art to formulate the polymer foam to suit the particular intended applications. In particular, it will be within the ability of those skilled in the art, given the benefit of this disclosure, to formulate polymer foams comprising chemically modified carbonaceous fillers, optionally along with additives such as any of those which are well-known for use in insulative polymer foams. Without wishing to be bound by theory, it is believed that particulate filler materials employed in prior filled polymer foams were preferentially located in the "struts" portion of the individual cells of the foam, rather than in the "windows" of the cells. It is believed that the foaming process in which polymer material is thinned to form the windows, causes prior known particulate filler materials to move from the window area into the struts area. In accordance with certain preferred embodiments of this invention, chemically modified carbonaceous fillers are employed which preferentially locate in the windows portion of the foam cells, rather than in the struts. Thus, in comparison to the use of, for example, carbon black particles of substantially the same particle size and structure, the use of chemically modified carbonaceous filler as disclosed here results in a higher particle density in the window portions of the polymer cell foam than would be achieved using such carbon black particulate filler. In other preferred embodiments, the chemically modified carbonaceous filler achieves better (i.e., more uniform) distribution within the foam and/or controls the cell size of the foam or the cell size distribution so as to provide better insulative properties.

The preferential locating of chemically modified carbonaceous particulates in the windows of the foam cells provides an additional benefit. Specifically, carbon black located in the foam cell windows is found to be more effective at reducing radiative thermal losses, through its action as an infra-red (IR) absorber. Because the thermal conductivity of particulate filler typically is substantially higher than the thermal conductivity of the polymer material, reducing the amount of particulate filler can reduce the thermal conductivity of the foam. Hence, by using chemically modified carbonaceous fillers which locate preferentially in the windows of the foam cells, a desired reduction in radiative loss can be accomplished with less particulate filler, thereby achieving also the desired reduction in solid-phase conductivity. In accordance with preferred embodiments, chemically modified carbonaceous filler is used in the polymer foams of the present invention in an amount less than twelve percent (12%) by weight of the foam (that is, a per unit weight of the total foam composition). More preferably, the chemically modified carbonaceous filler is used in an amount less than ten weight percent (10.0 wt. %), for example, one percent to eight percent (1% to 8%).

The polymer foam materials suitable. for use in the foams of the present invent include those currently known for insulative foam applications. Preferred polymer foams include polyurethane foams, polyisocyanurate foams and polystyrene foams. In certain preferred embodiments, such polymer foams are formed without chlorofluorocarbons (CFCs) and hydrochlorofluoro carbons (HCFCs). Rather, these preferred embodiments employ as blowing agents certain hydrocarbons, such as pentane, isopentane and cyclopentane. Thermal conductivity of polymer foams, such as polyurethane foams, formed using such hydrocarbon blowing agents typically have higher thermal conductivities than corresponding foams formed with CFCs or HCFCs. The hydrocarbon blowing agents, however, are believed to be environmentally advantageous over CFCs and HCFCs. In accordance with certain preferred embodiments of the present invention, the higher thermal conductivity of polymer foams formed with hydrocarbon blowing agents is reduced or overcome through the use of chemically modified carbonaceous fillers as disclosed herein.

In accordance with certain preferred embodiments, a method of insulating a structure is provided, especially a method of providing thermal insulation. A layer, for example, a sheet or block, of closed cell polymer foam in accordance with the foregoing disclosure, is employed as at least one component of a wall of the structure. Preferably a rigid polymer foam panel, e.g., a reaction injection molded polymer foam panel or an extruded polymer foam panel, is applied to a wall of the structure to be insulated. In this regard, the present invention is an improvement over the disclosure of U.S. Pat. No. 5,373,026 to Bartz et al, the entire disclosure of which is hereby incorporated by reference.

Similarly, the present invention is an improvement over the technology exemplified by U.S. Pat. No. 5,604,265 to DeVos et al regarding the preparation of fine-celled, closed-celled, rigid polyurethane or urethane-modified polyisocyanate foam. The entire disclosure of the DeVos et al patent is hereby incorporated by reference for its teaching of the preparation and use of fine-celled, closed-celled rigid foams. It will be within the ability of those skilled in the art, given the benefit of the disclosure herein of the present invention, to make and use polymer foam products incorporating chemically modified carbonaceous filler in lieu of the carbon black fillers suggested in the DeVos et al patent.

In accordance with certain preferred embodiments, polymer foam of the invention is made by mixing together two or more reactive polymer components, for example, a polyisocyanate component and a polyol component for making a polyurethane foam. The chemically modified carbonaceous filler employed in such preferred embodiments of the present invention can be dispersed into one or more such reactive components prior to mixing the reactive components together. Alternatively, the chemical chemically modified carbonaceous filler can be dispersed into the reactive components as they are mixed together.

In especially preferred embodiments, a closed-cell, rigid polymer foam incorporating such chemically modified material has thermal conductivity at least one percent and in certain especially preferred embodiments five percent or even ten or more percent better (i.e., lower) than a corresponding polymer foam without the filler. It also has better thermal insulating value than a corresponding polymer foam employing a corresponding unmodified carbonaceous particulate filler material in like amount. Preferably, the polymer foams have at least about _87_% closed cells, more preferably at least about _91_% closed cells. In accordance with certain preferred embodiments, rigid, closed-cell, polyurethane foam comprising chemically modified carbonaceous filler has cell windows which are about 0.5 microns in thickness. Especially preferred embodiments of this type employ chemically modified carbonaceous filler formed by chemically bonding to the surfaces of carbon black particulate a polymer moiety having an amine or alcohol functional group to provide reactivity or affinity to a polyol or isocyanate reactive component of such polyurethane foam. The polyurethane foam is formed by achieving excellent initial dispersion of the chemically modified carbonaceous filler into the appropriate reactive component of the foam.

In accordance with certain preferred embodiments, closed-cell, rigid polymer foam comprises chemically modified carbonaceous filler having chemically bonded polymer moieties carrying low surface energy groups attached to the surface of the particles. Without wishing to be bound by theory, it is presently understood that the low surface energy groups at the surface of the particles changes their wetting characteristics. These changes in surface energy are believed to drive the filler particles toward the gas/solid interface found primarily at the windows of the foam cells. In accordance with certain especially preferred embodiments, the chemically modified carbonaceous particulate filler bears alkyl, such as C1 to C20 groups, e.g. C1 to C8 groups, or halogenated alkyl groups, especially fluorinated alkyl groups, polyalkylene oxides, or polysiloxanes.

In accordance with certain preferred embodiments, rigid, closed-cell foams, e.g. polyurethane foams, are provided with cell sizes less than 200$\mu$, preferably about 150 to 200$\mu$. Chemically modified carbonaceous particulate fillers suitable for such preferred embodiments include those bearing surface functionality capable of generating gas to nucleate cell formation during foam manufacture, especially functional groups capable of generating gas at elevated temperatures. Especially preferred embodiments of this type include polyurethane foams incorporating chemically modified carbonaceous particulate filler bearing (that is, as-incorporated into the reactive polymer components) t-butylcarbonates or acylazides or the like. In accordance with certain alternative embodiments, the chemically modified carbonaceous particulate filler carries a surface coating of a substance which decomposes at elevated temperatures to generate gas. In accordance with yet other preferred embodiments of this type, rigid closed-cell polyurethane foams comprise particulate filler which is highly porous. Without wishing to be bound by theory, it is presently understood that the porous particles of such fillers trap gas which is released during the foam manufacturing process to nucleate foam cell formation. Exemplary chemical blacks of this type include chemically modified porous blacks, such as chemically modified BP2000™ carbon black, which is commercially available from Cabot Corporation.

The following polyurethane foam components are used in typical rigid polyurethane foams of the present invention:

1. Polyol or polyol blend with an average functionality of from 3 to 8 and with mean molecular weights of from about 150 to 1,600, and hydroxyl values (mg KOH/g) of 250 to 1,000. Polyols may be, for example polyether, modified polyether, or polyester polyols.

2. Polymeric MDI with an NCO value (%NCO by weight) of from 27 to 31, average functionality of 2.7 to 3.0, and viscosity of from 230 to 2700 mPa at 25° C.

3. Catalysts, such as tertiary amine (e.g., diaminobicyclooctane) or organometallic catalysts (e.g., dibutyltin dilaurate).

4. A surfactant, such as organosiloxanes or silicone-based surfactants, for example, polydimethylsiloxane-polyether graft copolymer surfactants.

5. Blowing agents such as CFC's, HCFCs, FC's, hydrocarbons, water, etc.

6. Optionally flame retardants.

An exemplary rigid polyurethane foam formulation suitable for filled polymer foam products of the present invention is prepared by blending components together in the proportions listed below.

| Component | Parts |
| --- | --- |
| Polyol (hydroxyl number of 750) | 100 |
| PMDI (NCO value of 31) | 182 |
| Surfactant | 0.1 to 5 |
| Amine Catalyst | 0.1 to 3 |
| Cyclopentane | 5 to 20 |
| Water | 0.1 to 5 |

Chemically modified carbonaceous filler as disclosed above can be added to the component list to prepare a foam with improved (i.e., lower) thermal conductivity. The chemically modified carbonaceous filler can be dispersed into either of the polymer reactants, i.e., into the polyol or into the isocyanate at any suitable loading level, e.g., a 6–12% loading, using any suitable mixing apparatus, e.g., a Silverson L4R high speed rotor/stator mixer. For example, a filler/isocyanate dispersion is mixed for 30 minutes using the high sheer head at maximum speed.

In certain preferred embodiments of the present invention, the chemically modified carbonaceous filler is prepared by chemically modifying the surface of a carbon black particulate material, as now further discussed. Certain chemically modified carbonaceous fillers suitable for use in the present invention can be formed by chemically treating carbon black particulate materials. Surface treatment of about 1 to 5 $\mu$mol/m$^2$ is preferred, with 4 $\mu$mol/m$^2$ being especially preferred in most cases, since this is presently understood to provide approximately full surface coverage of a typical carbon black material. The polymer moieties attached to the carbonaceous particles in such embodiments result, in certain preferred embodiments, from reaction of a suitably functionalized polymer reactant with suitably functionalized carbonaceous particles. Polymer reactants which can be functionalized for reaction with the carbonaceous particles include, for example, polyethylene, poly(vinylchloride), polyisobutylene, polycaprolactam (nylon), polyisoprene, polyamides, polycarbonates, polyelectrolytes, polyesters, polyethers, (polyhydroxy)benzenes, polyimides, polymers containing sulfur, polyolefins, polymethylbenzenes, polystyrene, styrene copolymers, acetal polymers, acrylic polymers, acrylonitrile polymers and copolymers, polyolefins containing halogen, fluoropolymers, ionomeric polymers, polymers containing ketone group(s), liquid crystal polymers, polyamideimides, polymers containing olefinic double bond(s), polyolefin copolymers, polyphenylene oxides, polyurethanes, thermoplastic elastomers, silicone polymers, alkyd, epoxy, and unsaturated polyester.

In accordance with preferred embodiments, the polymer reactant is selected from: fluoropolymer alkylene oxide polymer or polyether, most preferably fluoropropylene oxide polymers, having number average molecules weight of about 200 to 20,000, more preferably about 500 to 5000, for example, about 1000; alkylene oxide polymers or polyethers, most preferably propylene oxide polymers, having number average molecules weight of about 200 to 20,000, more preferably about 500 to 5000, for example, about 1300; and siloxanes having number average molecules weight of about 200 to 20,000, more preferably 500 to 5000, for example, about 1300.

The reactive functionality of the polymer reactant is selected to correspond to the reactive functionality of the carbonaceous particulate material, to yield the chemically bonded reaction product as discussed above. That is, the mutually reactive functionalities of the polymer reactant and the particulate in accordance with there preferred embodiments, yield a surface-modified carbonaceous particulate filler having polymer moieties chemically bonded (ironically or covalently) to the carbonaceous particles. As explained above, reference herein to chemically modified carbonaceous filler or particulates means carbonaceous filler which has polymer groups chemically bonded to the particulates, i.e., via valence orbital bonding to yield ironically or covalently bonded polymer moieties. In accordance with certain preferred embodiments, the surface modification for attachment of the functional groups is achieved by grafting the polymers to the surface of the carbon black via radical reactions. Exemplary radical reactions include the reaction of stabilized free radical polymers with carbon black, activated carbon, graphite, carbon fibers or fibrils. In accordance with other preferred embodiments, the surface modification is achieved by growing polymers from the surface of the carbonaceous particle using ionic or free radical polymerization techniques. These and other suitable surface modification techniques and materials and their suitability for use in the present invention will be apparent to those skilled in the art given the benefit of the present disclosure.

In accordance with certain preferred embodiments, carbon block is surface modified to chemically bond silicone moieties. In certain such embodiments the surface of the carbon black is first modified via a diazonium reaction that attaches (i.e., chemically bonds) negatively charged groups to the surface of carbon black (e.g. that of sulfanilic acid, for the attachment of benzosulfonate groups.) The surface of the carbon black is then further treated with positively charged amino-silicone compounds that will form ionic bonds with the negatively charged ionic groups present at the surface of the carbon black, and attach themselves to the carbon black. The aminosilicone groups can consist of either oligomeric silicones (e.g. 4-aminobutyldimethylmethoxysilane— $C_7H_{19}NOSi$) or polymeric silicones (e.g. Polydimethylsiloxane, aminopropyldimethyl terminated— $NH_2CH_2CH_2CH_2O[(CH_3)_2SiO]_yCH_2CH_2CH_2NH_2$), or copolymers having pendant amine groups. The treatment groups can also have single or double amine functionality. The amines can be primary, secondary, or tertiary (in which case, preferably, they are protonated to react) or quaternary salts (in which case they are inherently positively charged) that can be prepared by alkylation of the previous categories of amines.

These new surface modified carbon blacks can have a desired silicon content based on the selected treatment level. By modifying the surface of carbon black using this two-stage treatment procedure, the silicon-containing carbon black, in certain preferred embodiments, especially in polyurethane frames, will be found in higher concentrations at the cell faces of the foam than will conventional grades of carbon black. That is, the treated carbon black particles will have surfactant properties and preferentially migrate to the gas/liquid surface of the polyurethane as it foams, thus locating in the windows and improving the thermal insulation value of the polyurethane foam.

In alternative preferred embodiments, the surface modification is of carbon black or other chemically modified carbonaceous filler with silicon-based functional groups is accomplished through the covalent attachment of the oligomeric or polymeric silicones or siloxanes. Exemplary silicone surface modifying materials include, for example, Polydimethylsiloxanes, other organic siloxanes and block copolymers that contain other materials, such as alkylene oxides, for example.

Again, the surface modified particles can have a desired silicon content based on the selected treatment level.

In accordance with certain preferred embodiments, carbon black or other carbonaceous filler is surface modified to chemically bond poyalkylene oxide moieties. In certain such embodiments the surface of the carbon black is first modified via the diazonium reaction that attaches negatively charged groups to the surface of carbon black (e.g. sulfanilic acid for the attachment of benzolufonate groups. The surface of the carbon black is then further treated with polyalkylene oxide polymers containing positively charged groups (e.g. p-alphaaminoethylphenol propoxylate-N30) that will form ionic bonds with the negatively charged groups present at the surface of the carbon black and attach themselves to the carbon black. The black may also be modified via diazonium reaction that attaches positively charged groups to the surface of carbon black (e.g. 3-aminopyridime for the attachment of a pyridinium group). The surface of the carbon black can then be further treated with a polyalkylene oxide polymers containing negatively charged groups to form an ionic bond with the positively charged group present at the surface of the carbon black.

By modifying the surface of carbon black using this two-stage treatment procedure, the attachment group will allow for better dispersion in the foam making components (e.g. PMDI or Polyol) and will also allow for higher concentrations of carbon black at the cell faces of the foam compared to prior known fillers. That is, the treated carbon black particles will have surfactant properties and preferentially migrate to the gas/liquid surface of the polyurethane as it foams, thus locating in the cell windows and improving the thermal insulation value of the polyurethane/ polyisocyanurate foam. In alternative preferred embodiments, carbon block or other carbonaceous filler is chemically modified by covalent attachment of polymeric alkylene oxide groups to the carbon black.

In accordance with certain preferred embodiments, carbon black or other carbonaceous filler is surface modified by chemically bonding fluorinated polymer moieties to the particles. Improved dispersability, thermal insulation and flame retardance, in polyurethane or polyisocyanurate foams especially, is obtained. Suitable fluorinated polymers for use as reactants include fluorinated surfactants.

Preferred fluorinated materials contain as part of their structures a straight chain of difluoromethylene, diflouromethylene oxide, fluoroethylene oxide, or hexafluoropropylene oxide monomer, as well as short or long chain hydrocarbon and/or polyether segments. The Fluorinated materials will be attached to the surface of the carbon black either through ionic or covalent bonding. For attachment through ionic bonding the fluoropolymer preferably has a charged moiety, either positive or negative, in its molecular structure. The carbon black or other carbonaceous particle is surface treated to have oppositely charged moieties. For covalent attachment the fluoro-compound has, or is modified to possess a functional group that will allow for covalent bonding to the surface of the carbon black. Again, the filler particle is surface treated to have functional groups reactive with the functional groups of the fluoro-compound.

In the case of covalently bonded fluorinated polymers the carbon black or other carbonaceous filler to be modified need to have any special characteristics. However, in the case of ironically bonded fluorinated polymers, the surface of the carbon black or other carbonaceous filler preferably has already undergone treatment leaving it with a relatively stable and uniform charge. These surface functionalized material may be dispersed in either the Polyol or isocyanate side of the foam system.

These carbon black or other carbonaceous filler materials, when incorporated into rigid closed cell polyurethane foams, for example, will be found in higher concentrations at the cell faces of the foam than will conventional grades of carbon black. That is, more of the carbon black will be found at the gas/solid interface in the polyurethane foams containing the modified carbon materials. Moreover, this improved distribution of the modified carbon black will, in certain preferred embodiments, result in lower thermal conductivity of the polyurethane foam in comparison to polyurethane foam containing conventional carbon black. In addition, the high amounts of fluorine present in the final foam formulation serve to increase the flame retardance of the foam material.

In accordance with certain preferred embodiments, graphite, including, for example, modified synthetic graphite is employed. The chemical modification of the surface chemistry of the graphite, as disclosed here, provides treated graphites whose performance is superior to the corresponding untreated material. Specifically, the incorporation of such treated graphites yields insulating polymer foam materials with reduced thermal conductivity, or enhanced insulting performance, when compared to corresponding materials formed by incorporating the corresponding unmodified graphites. In a preferred method for preparing the chemically modified graphite, surface modification yields treated graphite material that exhibits superior dispersion in the foam when compared to the use of an unmodified graphite. Surface modification can also yield a higher concentration of graphite material in the cell faces or windows than results when using an unmodified graphite.

Methods for modifying the surface chemistry of graphite include chemically bonding materials to the surface by covalent or ionic bonds, preferably through surface treatment chemistry herein discussed with reference to carbon black and other filler materials.

Various types of materials may be used to modify the surface of graphite. Examples include, but are not limited to: Alkylene oxides, siloxanes, poly(acrylic acid) and derivatives such as poly(amides), poly(vinyl alcohols), fatty acids, ethoxylated fatty acids, and fatty acid esters, saturated and unsaturated hydrocarbons, fluorinated or perfluorinated chains, and copolymers comprising combinations of any of the above.

The above materials may contain or be terminated by primary, secondary, tertiary, or quaternary amines, and are thus capable of having as part of their structure a stable cation. The above materials may contain or be terminated by negatively charged moieties such as sulfates, phosphates, and carboxylates and are thus capable of having as part of their structure a stable anion. The above materials may also contain or be terminated by a primary aryl amine. The presence of an aryl amine moiety enables covalent attachment via the generation of the corresponding diazoium salt of the amine, such as described in U.S. Pat. No. 5,553,739 the entire disclosure of which is incorporated herein by reference. This same process is also useful for covalently attaching molecules containing as part of their structures stabilized charges. For example the attachment of a negatively charged benzene sulfonate group results form a diazonium treatment with Sulfanilic acid, Likewise, molecules with positive charges may be similarly attached. The resulting graphite product with charged molecules on the surface may then be subsequently treated with material containing a moiety of opposite charge, such as those listed above, yielding an ionic bond attachment between the premodified graphite and the material of interest.

Suitable reactants and methods preparing the chemically modifying carbonaceous filler, including, for example, suitable reactants and methods carbonaceous filler particles and correspondingly functionalizing the polymer reactants, are taught in the following documents, each of which is hereby incorporated herein by reference in its entirety:

International Application Number PCT/US97/08855 published by the World Intellectual Property Organization ("WIPO") as International Publication Number WO 97/47691; U.S. patent application Ser. No. 08/990715; U.S. patent application Ser. No. 09/210,370 filed on Dec. 14, 1998; U.S. patent application Ser. No. 60/104,117 filed on Oct. 13, 1998; U.S. patent application Ser. No. 08/968,299 filed on Nov. 12, 1997U.S. Pat. No. 6,068,688; U.S. patent application Ser. No. 08/962,244 filed on Oct. 31, 1997abandoned; U.S. patent application Ser. No. 08/899,263 filed on Jun. 3, 1998U.S. Pat. No. 6,009,318; U.S. patent application Ser. No. 09/089,363 and International Application Number PCT/US98/02518 published by WIPO as international Publication number WO98/34960.

It will be apparent to those skilled in the art from the foregoing disclosure of the present invention and from the detailed description of certain preferred embodiments, that numerous modifications and alternative embodiments are possible within the true scope and spirit of the invention. The following claims are intended to cover the true scope and spirit of the invention.

We claim:

1. Polymer foam composition comprising polymer foam and carbonaceous filler having polymer moieties chemically bonded to carbonaceous particulates.

2. The polymer foam composition of claim 1 wherein the carbonaceous filler comprises chemically modified carbonaceous particulates selected from carbon black, activated carbon, graphite, carbon fibers, fibrils and a mixture of any of them.

3. The polymer foam composition of claim 2 wherein the polymer moieties chemically bonded to the carbonaceous particulates are the reaction residue of reactively functionalized polymers selected from polyethylene, poly(vinylchloride), polyisobutylene, polystyrene, polycaprolactam (nylon), polyisoprene, polyamides, polycarbonates, polyelectrolytes, polyesters, polyethers, (polyhydroxy) benzenes, polyimides, polymers containing sulfur, polyolefins, polymethylbenzenes, polystyrene, styrene copolymers, acetal polymers, acrylic polymers, acrylonitrile polymers and copolymers, polyolefins containing halogen, fluoropolymers, ionomeric polymers, polymers containing ketone group(s), liquid crystal polymers, polyamideimides, polymers containing olefinic double bond(s), polyolefin copolymers, polyphenylene oxides, polyurethanes, thermoplastic elastomers, silicone polymers, alkyd, epoxy, unsaturated polyester.

4. The polymer foam composition of claim 1 wherein the polymer foam is polyurethane foam, polyisocyanurate, polystyrene or a mixture thereof.

5. The polymer foam composition of claim 1 wherein the polymer foam is rigid, closed-cell polymer foam.

6. The polymer foam composition in accordance with claim 1 wherein the carbonaceous filler is present in the polymer foam in an amount from 0.01 to 18 wt. %.

7. Rigid, closed-cell polymer foam comprising chemically modified carbonaceous particulate filler dispersed therein, the chemically modified carbonaceous particulate filler having polymer moieties chemically bonded to carbonaceous particulates selected from carbon black, activated carbon, graphite, carbon fibers, fibrils and a mixture of any of them, the polymer moieties carrying functional groups selected from isocyanates, acyl azides, alcohols, amines, thiols, and alkoxides.

8. The rigid, closed-cell polymer foam in accordance with claim 7 wherein the polymer foam is polyurethane foam, polyisocyanurate foam or polystyrene foam.

9. A reaction injection molding method of making polymer foam composition comprising polymer foam and carbonaceous filler having polymer moieties chemically bonded to carbonaceous particulates, said reaction injection molding method comprising the steps of:

dispersing the carbonaceous filler into a first reactant for the polymer foam, and then mixing a stream of the first reactant with a stream of second reactant for the polymer foam, wherein the polymer moieties are not stripped in substantial quantity from the carbonaceous particulates by the mixing step.

10. A thermal insulation product comprising rigid, closed-cell polymer foam and carbonaceous filler dispersed in the polymer foam and having polymer moieties chemically bonded to carbonaceous particulates.

11. A method of insulating a structure, comprising incorporating into a wall of the structure a rigid, closed-cell polymer foam comprising carbonaceous filler having polymer moieties chemically bonded to carbonaceous particulates.

12. The method of insulating a structure in accordance with claim 11 wherein the structure is an architectural structure or a refrigeration appliance.

* * * * *